United States Patent
Foster et al.

(10) Patent No.: US 8,401,654 B1
(45) Date of Patent: Mar. 19, 2013

(54) METHODS AND SYSTEMS FOR TREATING ONE OR MORE EFFECTS OF DEAFFERENTATION

(75) Inventors: Allison M. Foster, Santa Monica, CA (US); Rafael Carbunaru, Studio City, CA (US); Todd K. Whitehurst, Santa Clarita, CA (US); Kristen N. Jaax, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1489 days.

(21) Appl. No.: 11/479,487

(22) Filed: Jun. 30, 2006

(51) Int. Cl.
*A61N 1/00* (2006.01)
(52) U.S. Cl. .......................................... 607/45; 607/46
(58) Field of Classification Search ............... 607/45–46
See application file for complete search history.

(56) References Cited

U.S. PATENT DOCUMENTS

| | | | |
|---|---|---|---|
| 3,760,984 A | 9/1973 | Theeuwes | |
| 3,845,770 A | 11/1974 | Theeuwes et al. | |
| 3,916,899 A | 11/1975 | Theeuwes et al. | |
| 3,923,426 A | 12/1975 | Theeuwes | |
| 3,987,790 A | 10/1976 | Eckenhoff et al. | |
| 3,995,631 A | 12/1976 | Higuchi et al. | |
| 4,016,880 A | 4/1977 | Theeuwes et al. | |
| 4,036,228 A | 7/1977 | Theeuwes | |
| 4,111,202 A | 9/1978 | Theeuwes | |
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |
| 4,360,019 A | 11/1982 | Portner et al. | |
| 4,487,603 A | 12/1984 | Harris | |
| 4,562,751 A | 1/1986 | Nason et al. | |
| 4,586,509 A * | 5/1986 | Liss et al. ........................ | 607/46 |
| 4,627,850 A | 12/1986 | Deters et al. | |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,865,845 A | 9/1989 | Eckenhoff et al. | |
| 5,057,318 A | 10/1991 | Magruder et al. | |
| 5,059,423 A | 10/1991 | Magruder et al. | |
| 5,080,653 A | 1/1992 | Voss et al. | |
| 5,097,122 A | 3/1992 | Colman et al. | |
| 5,112,614 A | 5/1992 | Magruder et al. | |

(Continued)

FOREIGN PATENT DOCUMENTS

WO   WO 03/005465 A1   1/2003

OTHER PUBLICATIONS

Saitoh, Youichi et al.; Motor Cortex Stimulation for Deafferentation Pain; article; 2001; American Assoicatiation of Neurological Surgeons.

*Primary Examiner* — Nicole F Lavert
(74) *Attorney, Agent, or Firm* — Vista IP Law Group

(57) ABSTRACT

Methods of treating one or more effects of deafferentation within a patient include applying at least one stimulus to a stimulation site within the patient with an implanted stimulator in accordance with one or more stimulation parameters. The at least one stimulus is configured to treat one or more effects of deafferentation. Systems for treating one or more effects of deafferentation within a patient include a stimulator configured to apply at least one stimulus to a stimulation site within the patient in accordance with one or more stimulation parameters. The at least one stimulus is configured to treat one or more effects of deafferentation.

15 Claims, 13 Drawing Sheets

U.S. PATENT DOCUMENTS

| | | | | |
|---|---|---|---|---|
| 5,137,727 | A | 8/1992 | Eckenhoff | |
| 5,139,020 | A * | 8/1992 | Koestner et al. | 607/24 |
| 5,193,539 | A | 3/1993 | Schulman et al. | |
| 5,193,540 | A | 3/1993 | Schulman et al. | |
| 5,234,692 | A | 8/1993 | Magruder et al. | |
| 5,234,693 | A | 8/1993 | Magruder et al. | |
| 5,312,439 | A | 5/1994 | Loeb | |
| 5,417,717 | A * | 5/1995 | Salo et al. | 607/18 |
| 5,501,703 | A | 3/1996 | Holsheimer | |
| 5,728,396 | A | 3/1998 | Peery et al. | |
| 5,752,978 | A | 5/1998 | Chancellor | |
| 5,752,979 | A * | 5/1998 | Benabid | 607/72 |
| 5,792,187 | A * | 8/1998 | Adams | 607/5 |
| 5,938,688 | A | 8/1999 | Schiff | |
| 6,016,449 | A | 1/2000 | Fischell et al. | |
| 6,051,017 | A | 4/2000 | Loeb et al. | |
| 6,161,044 | A * | 12/2000 | Silverstone | 607/45 |
| 6,164,284 | A | 12/2000 | Schulman et al. | |
| 6,169,924 | B1 * | 1/2001 | Meloy et al. | 607/39 |
| 6,185,452 | B1 | 2/2001 | Schulman et al. | |
| 6,208,894 | B1 | 3/2001 | Schulman et al. | |
| 6,219,580 | B1 | 4/2001 | Faltys et al. | |
| 6,263,237 | B1 * | 7/2001 | Rise | 607/3 |
| 6,272,382 | B1 | 8/2001 | Faltys et al. | |
| 6,280,873 | B1 | 8/2001 | Tsukamoto | |
| 6,308,101 | B1 | 10/2001 | Faltys et al. | |
| 6,368,315 | B1 | 4/2002 | Gillis et al. | |
| 6,381,496 | B1 | 4/2002 | Meadows et al. | |
| 6,458,171 | B1 | 10/2002 | Tsukamoto | |
| 6,487,446 | B1 | 11/2002 | Hill et al. | |
| 6,505,075 | B1 | 1/2003 | Weiner | |
| 6,516,227 | B1 | 2/2003 | Meadows et al. | |
| 6,539,263 | B1 | 3/2003 | Schiff et al. | |
| 6,553,263 | B1 | 4/2003 | Meadows et al. | |
| 6,571,125 | B2 * | 5/2003 | Thompson | 604/20 |
| 6,620,151 | B2 | 9/2003 | Blischak et al. | |
| 6,650,943 | B1 * | 11/2003 | Whitehurst et al. | 607/39 |
| 6,666,845 | B2 | 12/2003 | Hooper et al. | |
| 6,721,603 | B2 | 4/2004 | Zabara et al. | |
| 6,740,072 | B2 | 5/2004 | Starkweather et al. | |
| 6,760,626 | B1 | 7/2004 | Boveja | |
| 6,770,067 | B2 | 8/2004 | Lorenzen et al. | |
| 6,862,479 | B1 * | 3/2005 | Whitehurst et al. | 607/39 |
| 6,885,895 | B1 * | 4/2005 | Whitehurst et al. | 607/39 |
| 7,302,296 | B1 * | 11/2007 | Hoffer | 607/48 |
| 2001/0046625 | A1 | 11/2001 | Ruth, II et al. | |
| 2001/0053476 | A1 | 12/2001 | Ruth et al. | |
| 2001/0053885 | A1 * | 12/2001 | Gielen et al. | 604/20 |
| 2004/0106953 | A1 * | 6/2004 | Yomtov et al. | 607/3 |
| 2004/0122477 | A1 * | 6/2004 | Whitehurst et al. | 607/9 |
| 2004/0127942 | A1 * | 7/2004 | Yomtov et al. | 607/3 |
| 2005/0143789 | A1 * | 6/2005 | Whitehurst et al. | 607/46 |
| 2005/0154435 | A1 * | 7/2005 | Stern et al. | 607/116 |
| 2005/0222628 | A1 * | 10/2005 | Krakousky | 607/3 |
| 2006/0095088 | A1 * | 5/2006 | De Ridder | 607/48 |

\* cited by examiner

METHODS AND SYSTEMS FOR TREATING ONE OR MORE EFFECTS OF DEAFFERENTATION

BACKGROUND

Deafferentation may be defined as a loss of sensory input from a portion of the body and is usually caused by an interruption between the brain or central nervous system and the peripheral sensory nerve fibers that innervate that portion of the body. Amputations and similar injuries in which a portion of the body is removed often give rise to deafferentation with respect to the portion of the body that is lost. Additionally, brachial plexus injuries, spinal cord injuries, and strokes are common causes of deafferentation.

The loss of sensory input produces compensatory changes in associated portions of the central nervous system. These changes often produce aberrant sensory signals. For instance, patients who have had a limb amputated commonly complain of "phantom limb syndrome," in which painful, itching, or tactile sensations are perceived to arise in the missing extremity.

A number of theories exist as to the cause of deafferentation pain. One theory proposes that the pain is likely due to neuromas—painful nodular proliferations of nerve tissue that result from the futile attempt of a proximal nerve fiber to reunite with its corresponding severed distal portion. Reorganization of A- and C-fiber terminals in the spinal cord is another possible cause of deafferentation pain.

Another possible cause of deafferentation pain involves neural plasticity and reorganization of brain function following deafferentation. Cortical and subcortical maps show that areas within the brain representing the damaged structure shrink while neighboring areas expand following deafferentation. Moreover, brain imaging studies have shown a strong correlation between the amount of somotosensory cortex reorganization and deafferentation pain.

A limited number of treatments for deafferentation pain have been developed. Traditional analgesics are usually ineffective at relieving deafferentation pain. However, anticonvulsants and antidepressants have shown limited success in managing the pain. Chronic epidural analgesia has also been shown to prevent some types of deafferentation pain. However, none of these treatments have been shown to be completely effective in treating deafferentation pain.

SUMMARY

Methods of treating one or more effects of deafferentation within a patient include applying at least one stimulus to a stimulation site within the patient with an implanted stimulator in accordance with one or more stimulation parameters. The at least one stimulus is configured to treat one or more effects of deafferentation.

Systems for treating one or more effects of deafferentation within a patient include a stimulator configured to apply at least one stimulus to a stimulation site within the patient in accordance with one or more stimulation parameters. The at least one stimulus is configured to treat one or more effects of deafferentation.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for treating one or more effects of deafferentation within a patient are described herein. An implanted stimulator is configured to apply at least one stimulus to a stimulation site within the patient in accordance with one or more stimulation parameters. As used herein and in the appended claims, the "treating" or "treatment of" the effects of deafferentation will be construed to include anything effective to minimize, ameliorate, or abrogate a cause or symptom of the effects of deafferentation. In some examples, the stimulus may be configured to treat the effects of deafferentation by mimicking sensory input to the brain. It is believed that the mimicked sensory input provided by the stimulator to the brain prevents compensatory neural reorganization within the brain and thereby prevents or alleviates one or more effects of deafferentation. In other examples, the stimulus may be effective to prevent the formation of neuromas or the reorganization of nerve fibers in the central nervous system.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment.

The appearance of the phrase "in one embodiment" in various places in the specification are not necessarily all referring to the same embodiment.

Figure 1A:
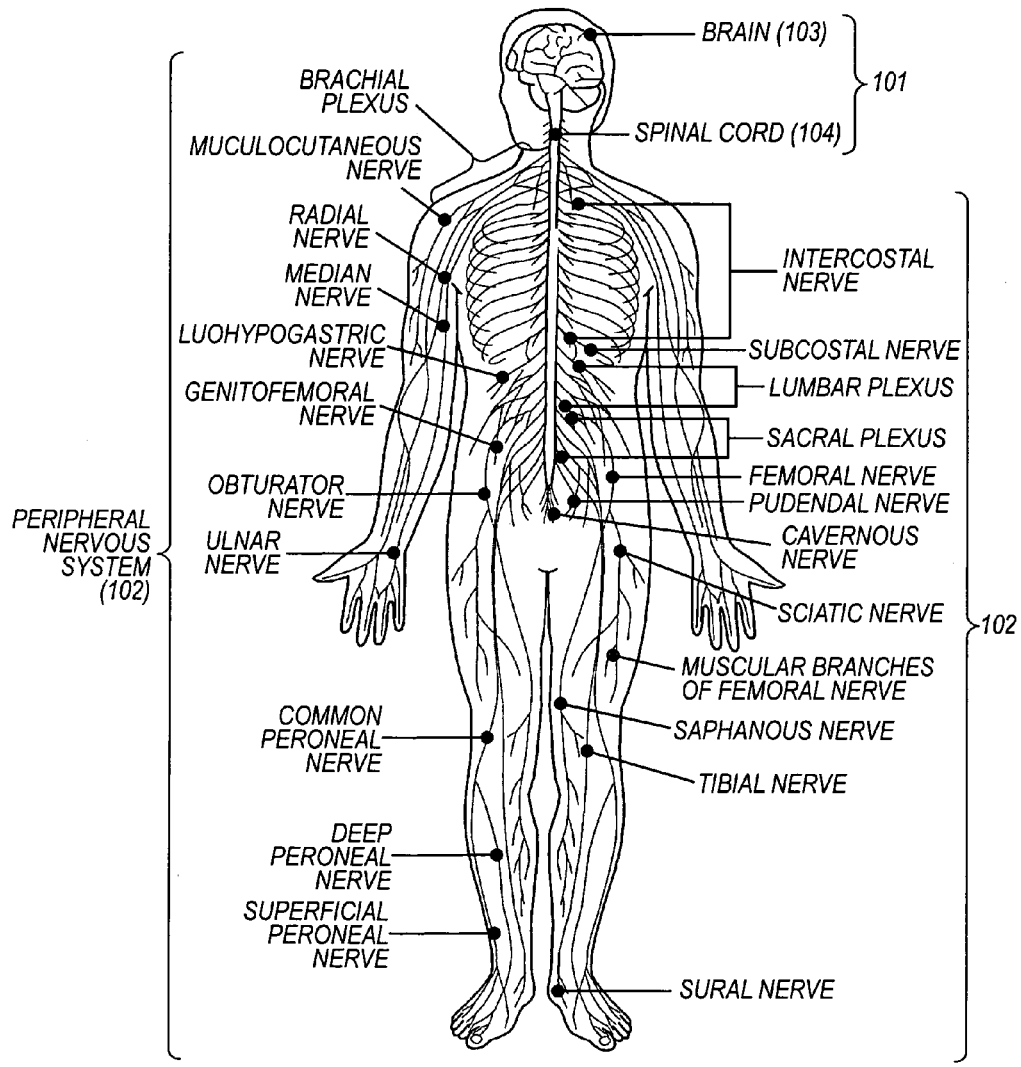
FIG. 1A is a diagram of the human nervous system.

Before discussing the present methods and systems for treating the effects of deafferentation, a brief overview of the human nervous system and brain will be given. FIG. 1A is a diagram of the human nervous system. The nervous system is divided into a central nervous system (101) and a peripheral nervous system (102). The central nervous system (101) includes the brain (103) and the spinal cord (104). The peripheral nervous system (102) includes a number of nerves that branch from various regions of the spinal cord (104). For example, the peripheral nervous system (102) includes, but is not limited to, the brachial plexus, the musculocutaneous nerve, the radial nerve, the median nerve, the iliohypogastric nerve, the genitofemoral nerve, the obturator nerve, the ulnar nerve, the peroneal nerve, the sural nerve, the tibial nerve, the saphenous nerve, the femoral nerve, the sciatic nerve, the cavernous nerve, the pudendal nerve, the sacral plexus, the lumbar plexus, the subcostal nerve, and the intercostal nerves.

The peripheral nervous system (102) may be further divided into the somatic nervous system and the autonomic nervous system. The somatic nervous system is the part of the peripheral nervous system (102) associated with the voluntary control of body movements through the action of skeletal muscles. The somatic nervous system consists of afferent fibers which receive information from external sources and efferent fibers which are responsible for muscle contraction.

Figure 1B:
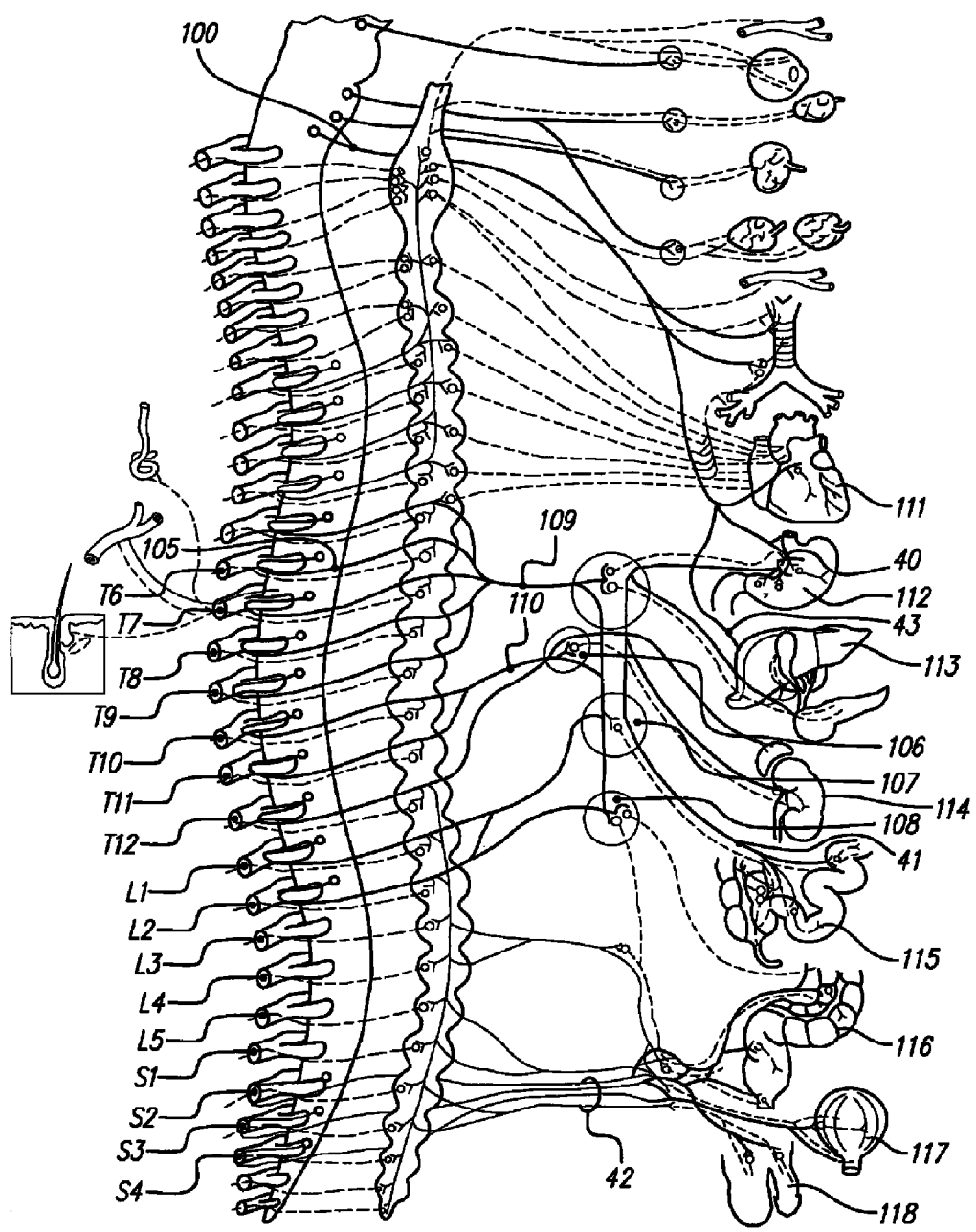
FIG. 1B illustrates the autonomic nervous system.

The autonomic nervous system, on the other hand, regulates the involuntary action of various organs and is divided into the sympathetic nervous system and the parasympathetic nervous system. FIG. 1B illustrates the autonomic nervous system. For example, FIG. 1B shows the following structures of the parasympathetic nervous system: the anterior or posterior vagus nerves (100), the hepatic branch (43) of the vagus nerve, the celiac branch (40) of the vagus nerve, the gastric branch (41) of the vagus nerve, and branches of the pelvic plexus (42).

FIG. 1B also shows the following structures of the sympathetic nervous system: the sympathetic afferent fibers (105) that exit the spinal cord at spinal levels T6, T7, T8, and T9; the sympathetic ganglia (e.g., the celiac ganglia (106) and its subsidiary plexuses, the superior mesenteric ganglia (107), and the inferior mesenteric ganglia (108)); the greater splanchnic nerve (109); and the lesser splanchnic nerve (110).

FIG. 1B also shows a number of organs that are controlled by the autonomic nervous system, including, but not limited to, the heart (111), stomach (112), liver (113), kidney (114), large intestines (115), small intestines (116), bladder (117), and reproductive organs (118).

Figure 2A:
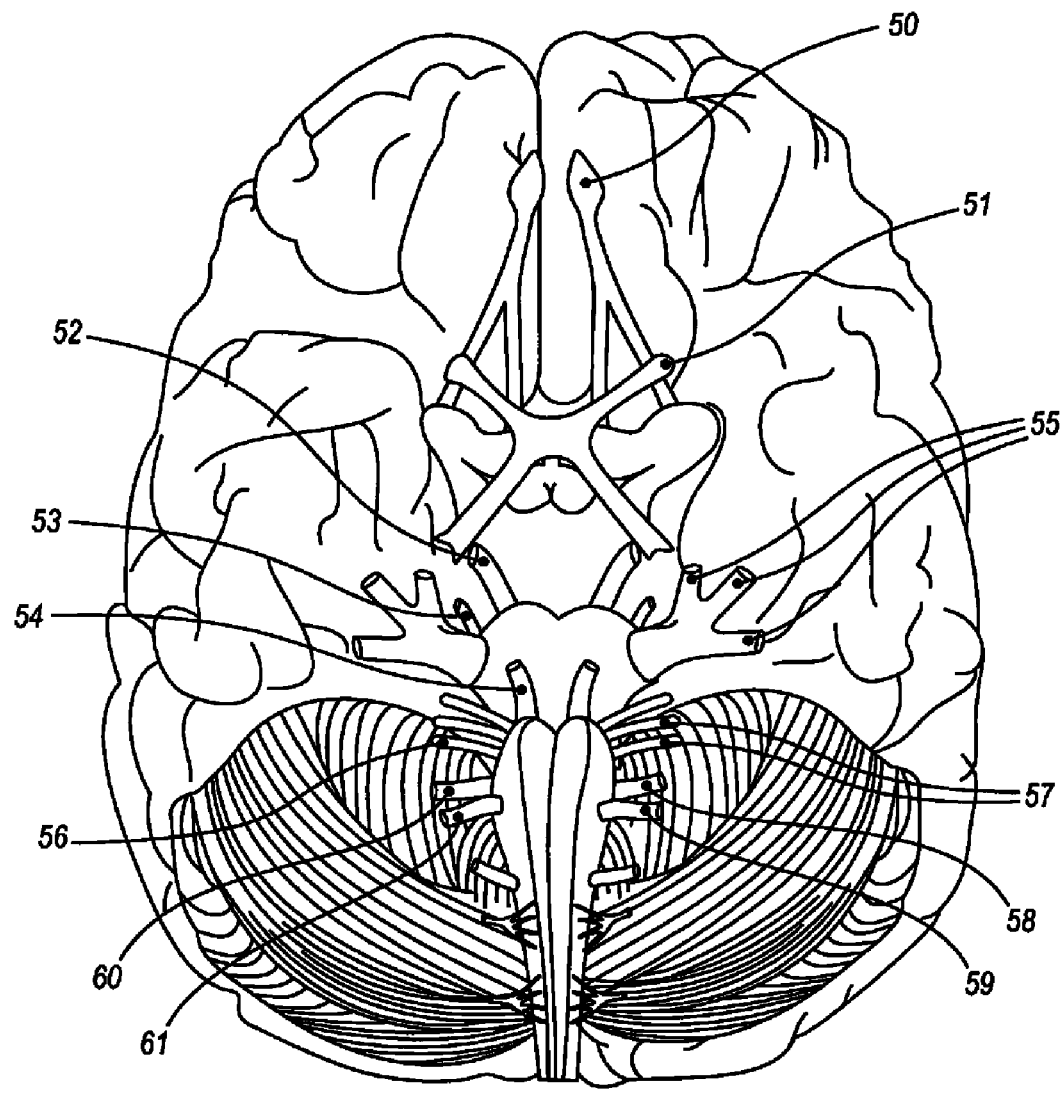
FIG. 2A is a perspective top view of the brain and illustrates a number of cranial nerves.

FIG. 2A is a perspective top view of the brain and illustrates a number of cranial nerves. The cranial nerves include twelve pairs of nerves that emanate from the nervous tissue of the brain: the olfactory (50), optic (51), oculomotor (52), trochlear (53), abducent (54), trigeminal (55), facial (56), auditory (57), glossopharyngeal (58), vagus (59), hypoglossal (60), and accessory (61) nerves. These nerves control various muscles, organs, and other tissue throughout the body. They are also responsible for carrying nerve impulses from these muscles and organs back to the brain.

Figure 2B:
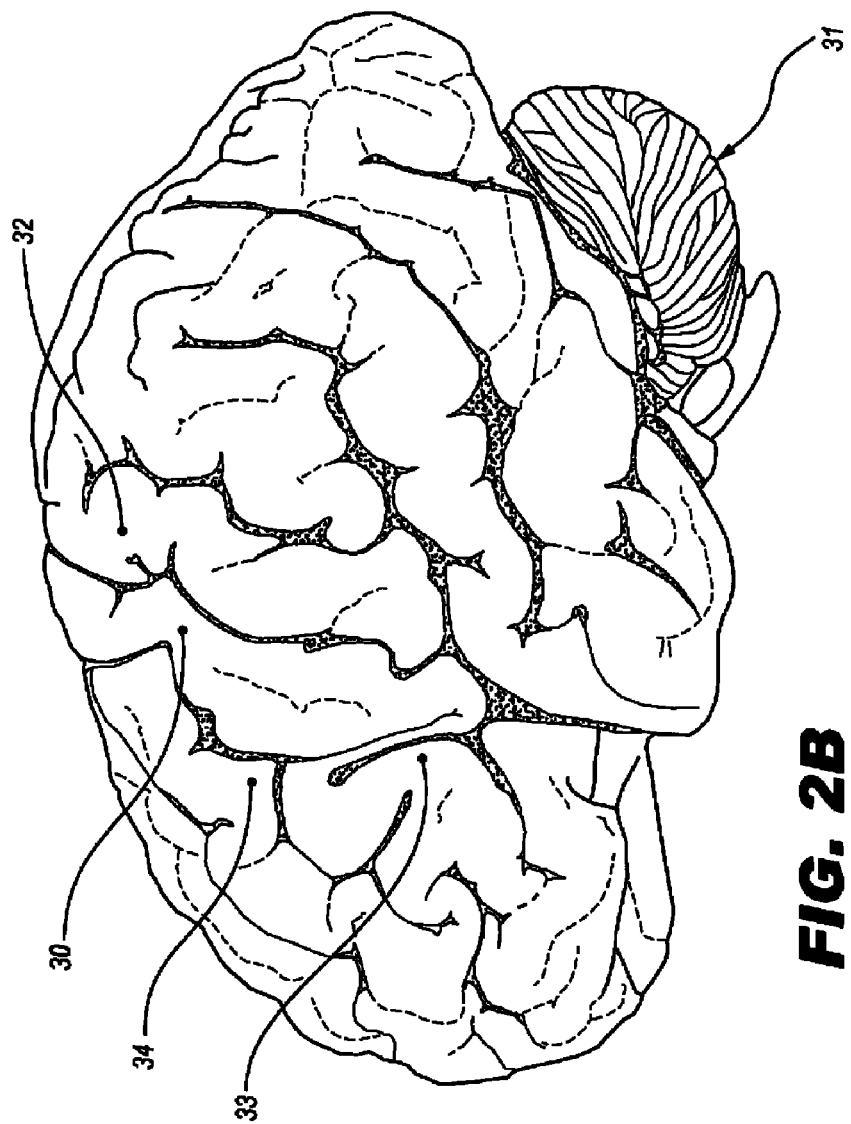
FIG. 2B depicts the lateral surface of the brain.

FIG. 2B depicts the lateral surface of the brain. The cerebral cortex (30) is the outermost layer of the brain and is involved in many complex brain functions including, but not limited to, memory, attention, perceptual awareness, thinking, language, and consciousness. Also shown in FIG. 2B are the somatosensory cortex (32), premotor cortex (33), and supplementary motor cortex (34). These structures are also involved in controlling motor movements.

FIG. 2B also shows the cerebellum (31). The cerebellum (31) is located in the posterior of the head and is responsible for the coordination of movement and balance. The cerebellum (31) includes the superior, middle and/or inferior cerebellar peduncles (not shown) as well as the interpositus nucleus (not shown).

Figure 2C:
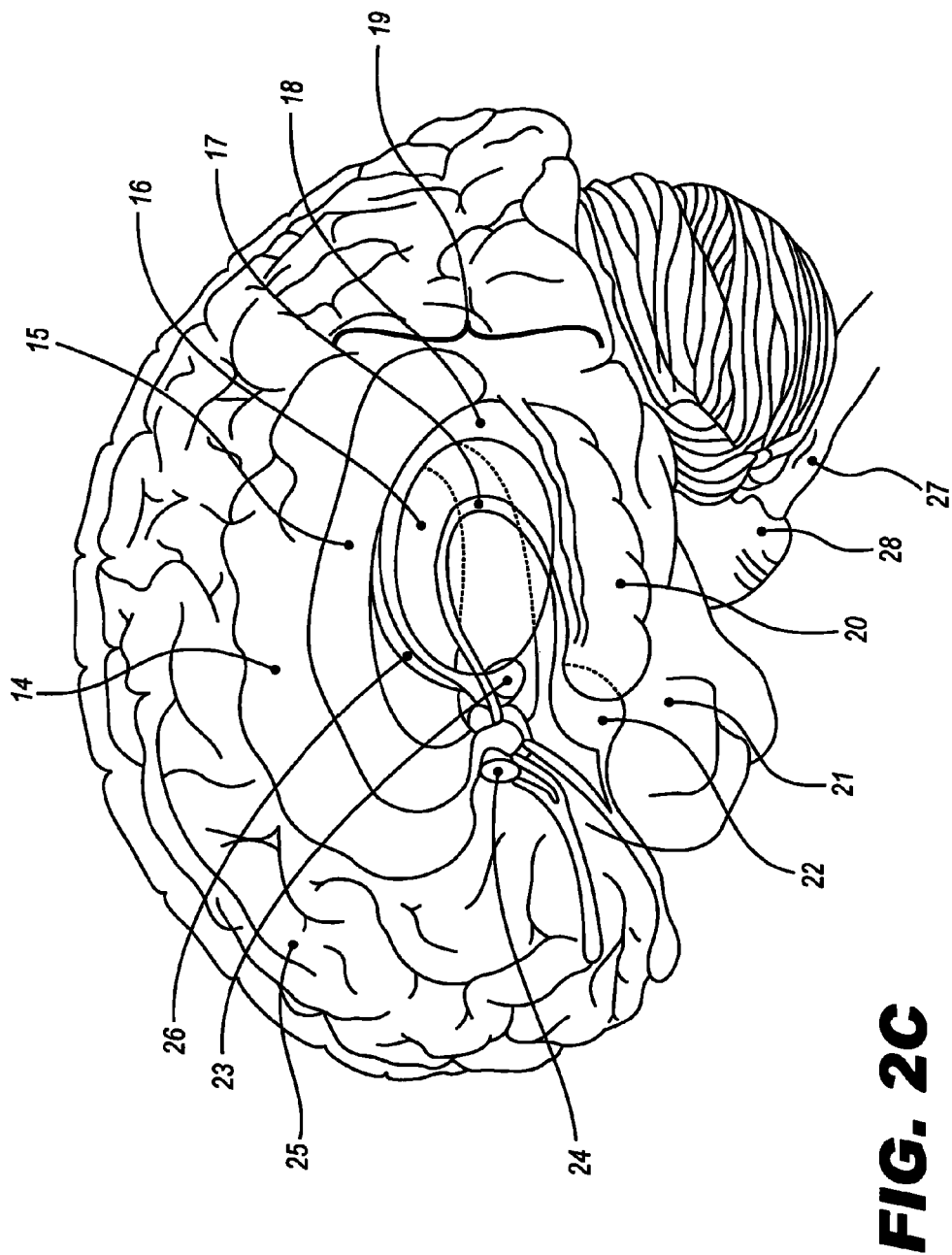
FIG. 2C is a perspective lateral view of the brain.

FIG. 2C is a perspective lateral view of the brain and depicts various structures of the limbic system. The limbic system is involved with emotion formation, learning, and memory. As shown in FIG. 2C, the limbic system includes several subcortical structures such as, but not limited to, the cingulate gyrus (14), corpus collosum (15), thalamus (16), stria terminalis (17), caudate nucleus (18), basal ganglia (19), hippocampus (20), entorhinal cortex (21), amygdala (22), mammillary body (23), medial septal nucleus (24), prefrontal cortex (25), and formix (26).

FIG. 2C also shows the brainstem (27). It extends from the base of the brain to the spinal cord. Nerve fibers extending from the brain to the spinal cord pass through the brainstem (27) and cross the midline at a location known as the decussation of the pyramids. The brainstem (27) includes the pons (28), which is a mass of nerve tissue that coordinates the activities of the various lobes of the brain.

Figure 3:
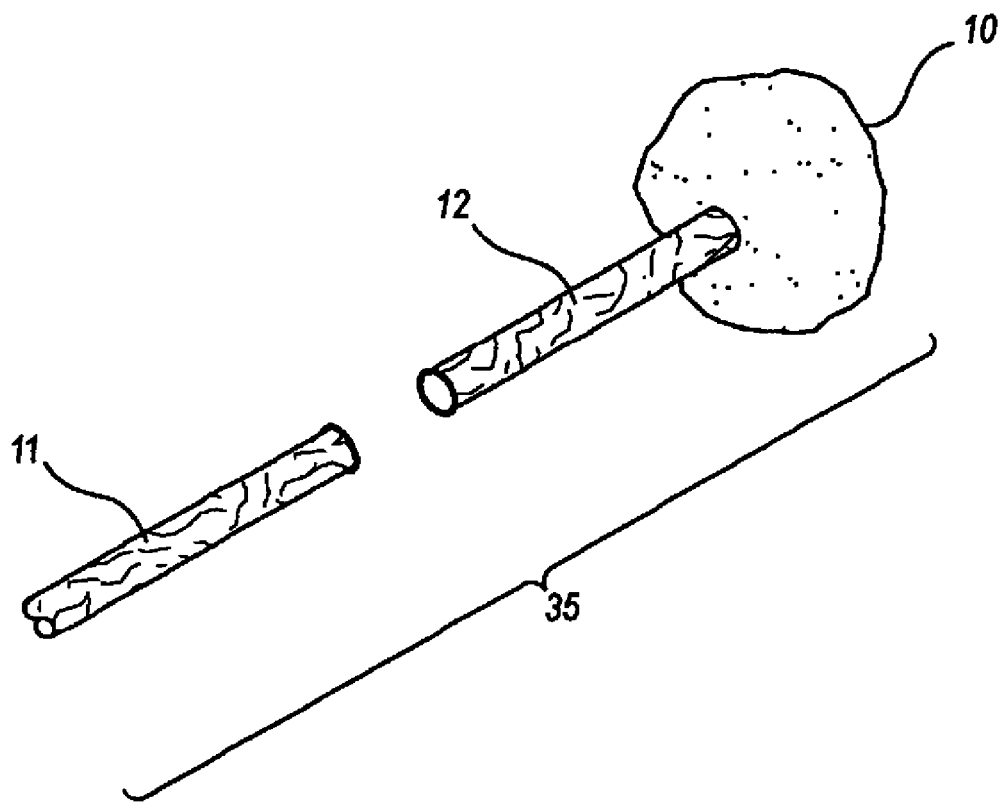
FIG. 3 illustrates an exemplary deafferentated nerve.

FIG. 3 illustrates an exemplary deafferentated nerve (35). In this context, a deafferentated nerve is a nerve that for any reason cannot, on a temporary or permanent basis, carry nerve signals from a particular innervated portion of the body to the brain or central nervous system. As indicated above, deafferentation may be caused by amputation, injury, stroke, or any other traumatic event with or without the loss of a body part. The deafferentated nerve (35) shown in FIG. 3 has been completely severed for illustrative purposes only. It will be recognized that the deafferentated nerve (35) may alternatively be inflamed, compressed, degenerated, or otherwise damaged.

As shown in FIG. 3, the deafferentated nerve (35) includes a proximal nerve portion (11) and a distal nerve portion (12). The proximal nerve portion (11) connects to the central nervous system (101; FIG. 1A) and the distal nerve portion (12) connects to an end organ (10) or other innervated portion of the body. For example, the end organ (10) may include an amputated extremity, a removed organ, a blood vessel, tissue, or any other structure within the body.

As mentioned, deafferentation may cause a patient to experience pain or phantom limb syndrome. Deafferentation may also cause a patient to experience phantom auditory experiences, phantom visual effects, or other undesirable or debilitating symptoms. Hence, as used herein and in the appended claims, the terms "deafferentation effects" and "effects of deafferentation" will be used interchangeably to refer to any pain, phantom limb syndrome, phantom auditory experiences, deafness, phantom visual effects, blindness, or other adverse symptom or experience caused by deafferentation.

For example, pain caused by deafferentation includes, but is not limited to, phantom limb pain, post-stroke pain, brachial plexus injury-related pain, spinal cord injury pain, and other pain associated with the interruption of peripheral sensory nerve fibers. Deafferentation pain accompanies a majority of extremity amputations and can also appear following removal of other parts of the body such as, but not limited to, a breast, rectum, reproductive organ, tooth, bladder, colon, or stomach.

Phantom limb syndrome may include, but is not limited to, any painful, itching, or tactile sensations that are perceived to arise in a missing extremity. Phantom limb syndrome is often experienced by a patient following the loss of an extremity or removal of an organ.

An exemplary phantom auditory experience is known as tinnitus, which is characterized by a ringing in the ears in the absence of any actual sound or auditory stimuli. Severe tinnitus may also be accompanied by the distortion of actual sounds in addition to the perception of the ringing sounds that are not actually occurring.

Exemplary phantom visual effects include, but are not limited to, Charles Bonnet syndrome and visual hallucinations. These phantom visual effects are often caused by deafferentation of the visual cortex.

It is believed that the above-listed effects of deafferentation are at least in part due to compensatory neural reorganization within the brain following deafferentation. The brain is a plastic organ. In other words, it is capable of reorganizing its neural connections in response to changes in bodily function, injury, or development. As a result, the brain attempts to compensate for deafferentation by reorganizing neural structure within the area responsible for the portion of the body affected by the deafferentation. Evidence to this effect includes cortical and subcortical maps which show that the areas within the brain representing or corresponding to a structure affected by deafferentation shrink while the neighboring areas expand following deafferentation.

Hence, it is believed that one or more effects of deafferentation may be treated by preventing compensatory neural reorganization within the brain. In some examples, as will be explained in more detail below, compensatory neural reorganization within the brain may be prevented by applying a stimulus to a deafferentated nerve, a location along the spinal cord corresponding to the deafferentated nerve, and/or a location within the brain that controls the structure experiencing deafferentation. The stimulus may be configured to mimic sensory input normally carried via the deafferentated nerve to prevent the brain from reorganizing its neural connections in an attempt to compensate for the deafferentation. As used herein and in the appended claims, the term "stimulus" will be broadly interpreted and may include an electrical stimulation current, one or more drugs, gene infusion, chemical stimulation, thermal stimulation, electromagnetic stimulation, mechanical stimulation, and/or any other suitable stimulus.

Consequently, as will be described in more detail below, a stimulator may be implanted within a patient and configured to deliver a stimulus to one or more stimulation sites to treat the effects of deafferentation. As used herein, and in the appended claims, the term "stimulator" will be used broadly to refer to any device that delivers a stimulus at a stimulation site to treat one or more deafferentation effects. Thus, the term "stimulator" includes, but is not limited to, a stimulator, microstimulator, implantable pulse generator (IPG), system control unit, cochlear implant, deep brain stimulator, drug pump, or similar device.

The stimulation site referred to herein may include a location along a deafferentated nerve, within the brain, or along the spinal cord. For example, the stimulation site may include any of the peripheral nerves or cranial nerves described above. Additionally or alternatively, the stimulation site may include one or more of the following locations within the brain: any area within, on, or in the vicinity of the temporal lobe; frontal lobe; occipital lobe; parietal lobe; limbic system; cerebellum; brainstem; cerebral cortex; cochlear nerve; visual cortex; optic radiations; Brodmann's areas 17, 18, and 19; superior olivary complex; inferior colliculus; auditory cortex; or cerebral ventricle.

Figure 4:
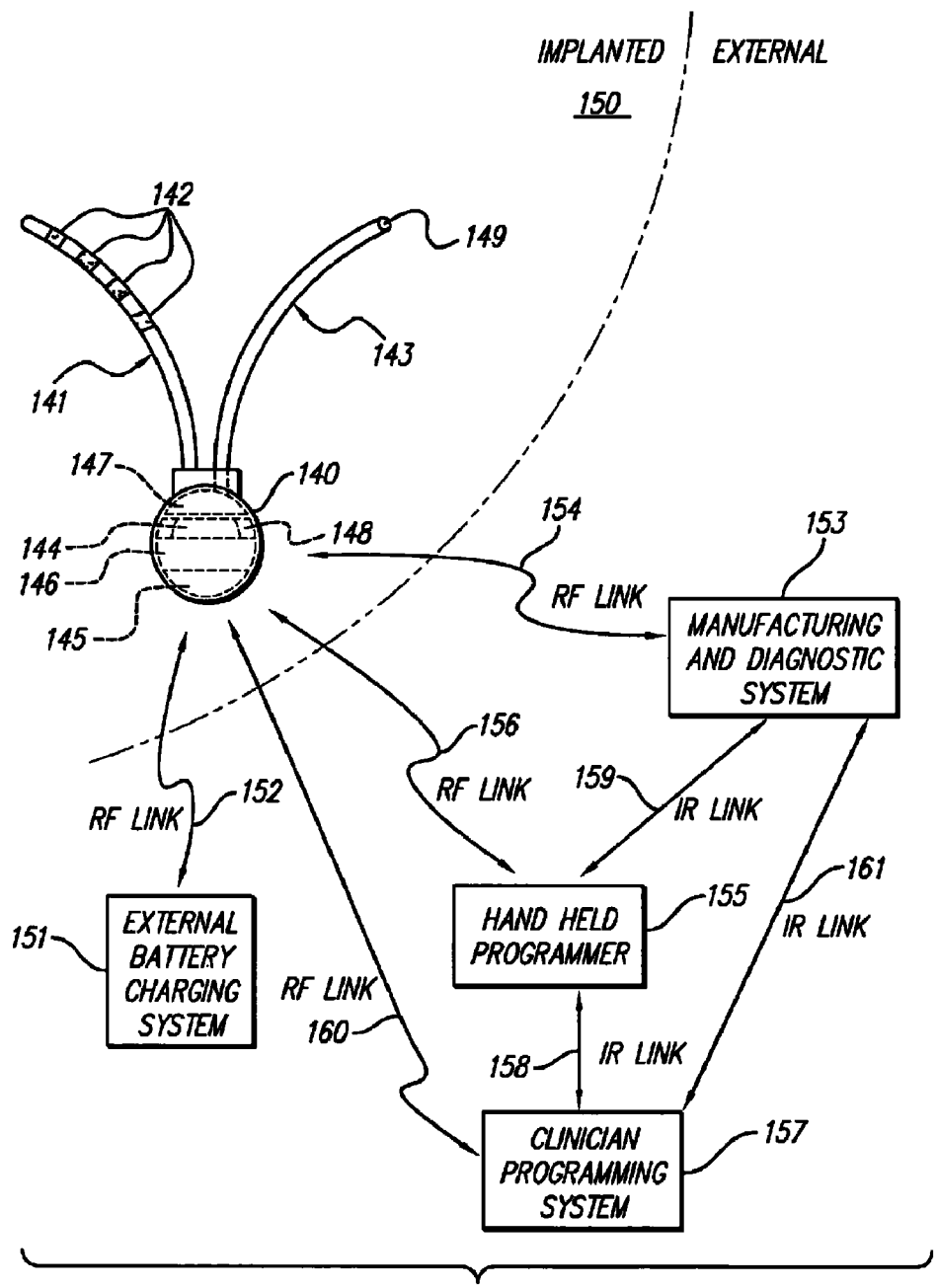
FIG. 4 illustrates an exemplary stimulator that may be used to apply a stimulus to a stimulation site within a patient to treat the effects of deafferentation according to principles described herein.

To facilitate an understanding of the methods of treating one or more deafferentation effects, a more detailed description of the stimulator and its operation will now be given with reference to the figures. FIG. 4 illustrates an exemplary stimulator (140) that may be implanted within a patient (150) and used to apply a stimulus to a stimulation site, e.g., an electrical stimulation of the stimulation site, an infusion of one or more drugs at the stimulation site, or both. The electrical stimulation function of the stimulator (140) will be described first, followed by an explanation of the possible drug delivery function of the stimulator (140). It will be understood, however, that the stimulator (140) may be configured to provide only electrical stimulation, only drug stimulation, both types of stimulation or any other type of stimulation as best suits a particular patient.

The exemplary stimulator (140) shown in FIG. 4 is configured to provide electrical stimulation to a stimulation site within a patient and may include a lead (141) having a proximal end coupled to the body of the stimulator (140). The lead (141) also includes a number of electrodes (142) configured to apply an electrical stimulation current to a stimulation site. The lead (141) may include any number of electrodes (142) as best serves a particular application. The electrodes (142) may be arranged as an array, for example, having at least two or at least four collinear electrodes. In some embodiments, the electrodes are alternatively inductively coupled to the stimulator (140). The lead (141) may be thin (e.g., less than 3 millimeters in diameter) such that the lead (141) may be positioned near a stimulation site. In some alternative examples, as will be illustrated in connection with FIG. 5, the stimulator (140) is leadless.

As illustrated in FIG. 4, the stimulator (140) includes a number of components. It will be recognized that the stimulator (140) may include additional or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their respective entireties. Other battery construction techniques that may be used to make a power source (145) include those shown, e.g., in U.S. Pat. Nos. 6,280,873; 6,458,171; and U.S. Publications 2001/0046625 A1 and 2001/0053476 A1, all of which are incorporated herein by reference in their respective entireties. Recharging may be performed using an external charger.

The stimulator (140) may also include a coil (148) configured to receive and/or emit a magnetic field (also referred to as a radio frequency (RF) field) that is used to communicate with, or receive power from, one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into the stimulation site.

Additionally, if multiple external devices are used in the treatment of a patient, there may be some communication among those external devices, as well as with the implanted stimulator (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140) may alternatively or additionally be configured to produce multipolar stimulation including, but not limited to, bipolar or tripolar stimulation.

In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing data used by the stimulator (140). The programmable memory (146) may include any type of memory unit such as, but not limited to, random access memory (RAM), static RAM (SRAM), flash memory, a hard drive, or the like. The programmable memory unit (146) may be located within the stimulator (140), as shown in FIG. 4. Additionally or alternatively, the programmable memory unit (146) may be included in a component located external to the patient and/or in another implanted device communicatively coupled with the stimulator (140).

In some examples, the programmable memory unit (146) may be programmed to store one or more stimulation parameters. As will be described in more detail below, the stimulation parameters may include, but are not limited to, electrical stimulation parameters, drug stimulation parameters, and other types of stimulation parameters.

In some examples, the stimulator (140) may be configured to generate at least one stimulus in accordance with one or more of the stimulation parameters stored within the programmable memory unit (146). For example, the stimulation parameters may at least partially control the stimulator (140) and cause the stimulator (140) to generate an electrical stimulation current, infuse one or more drugs at a stimulation site, or generate any other type of stimulation as best serves a particular application. It will be recognized that the stimulator (140) may include any combination of circuitry and/or processors configured to generate the at least one stimulus in accordance with one or more of the stimulation parameters.

Hence, a patient, clinician, or other user of the stimulator (140) may adjust the stimulation parameters such that the stimulation applied by the stimulator (140) is safe and efficacious for treatment of a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation or vice versa. Alternatively, the different types of stimulation may be applied at different times or with only some overlap.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different stimulation sites and/or different patients. Thus, in some embodiments, the stimulation parameters may be adjusted by the patient, a clinician, or other user of the stimulator (140) as best serves the particular stimulation site or patient being treated. The stimulation parameters may also be automatically adjusted by the stimulator (140), as will be described below. For example, the stimulator (140) may increase excitement of a stimulation site, for example, by applying a stimulation current having a relatively low frequency (e.g., less than 100 Hz). The stimulator (140) may also decrease excitement of a stimulation site by applying a relatively high frequency (e.g., greater than 100 Hz). The stimulator (140) may also, or alternatively, be programmed to apply the stimulation current to a stimulation site intermittently or continuously.

Additionally, the exemplary stimulator (140) shown in FIG. 4 is configured to treat the effects of deafferentation by applying one or more drugs at a stimulation site within a patient. In some examples, such drugs may be effective to prevent or discourage the brain or other structures of the central nervous system from attempting to compensate for the deafferentation. In other examples, such drugs may be effective to prevent the formation of neuromas or the reorganization of A- and C-fiber terminals in the spinal cord. For these purposes, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at the stimulation site. In some embodiments, the stimulator (140) may include multiple catheters (143) and/or pumps (147) for storing and infusing dosages of the one or more drugs at the stimulation site.

The pump (147) or controlled drug release device described herein may include any of a variety of different drug delivery systems. Controlled drug release devices based upon a mechanical or electromechanical infusion pump may be used. In other examples, the controlled drug release device may include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

The one or more drugs that may be applied to a stimulation site to treat the effects of deafferentation may have an excitatory effect on the stimulation site. Additionally or alternatively, the one or more drugs may have an inhibitory effect on the stimulation site to treat the effects of deafferentation. Exemplary excitatory drugs that may be applied to a stimulation site to treat the effects of deafferentation include, but are not limited to, at least one or more of the following: an excitatory neurotransmitter (e.g., glutamate, dopamine, norepinephrine, epinephrine, acetylcholine, serotonin); an excitatory neurotransmitter agonist (e.g., glutamate receptor agonist, L-aspartic acid, N-methyl-D-aspartic acid (NMDA), bethanechol, norepinephrine); an inhibitory neurotransmitter antagonist(s) (e.g., bicuculline); an agent that increases the level of an excitatory neurotransmitter (e.g., edrophonium, Mestinon); and/or an agent that decreases the level of an inhibitory neurotransmitter (e.g., bicuculline).

Exemplary inhibitory drugs that may be applied to a stimulation site to treat the effects of deafferentation include, but are not limited to, at least one or more of the following: an inhibitory neurotransmitter(s) (e.g., gamma-aminobutyric acid, a.k.a. GABA, dopamine, glycine); an agonist of an inhibitory neurotransmitter (e.g., a GABA receptor agonist such as midazolam or clondine, muscimol); an excitatory neurotransmitter antagonist(s) (e.g. prazosin, metoprolol, atropine, benztropine); an agent that increases the level of an inhibitory neurotransmitter; an agent that decreases the level of an excitatory neurotransmitter (e.g., acetylcholinesterase, Group II metabotropic glutamate receptor (mGluR) agonists such as DCG-IV); a local anesthetic agent (e.g., lidocaine); and/or an analgesic medication. It will be understood that some of these drugs, such as dopamine, may act as excitatory neurotransmitters in some stimulation sites and circumstances, and as inhibitory neurotransmitters in other stimulation sites and circumstances.

Additional or alternative drugs that may be applied to a stimulation site to treat the effects of deafferentation include, but are not limited to, neurotrophic factors (e.g., brain derived neotrophic factors (BDNF) and glial cell line derived neurotrophic factors (GDNF)), steroids, antibiotics, anticonvulsants, antidepressants, and gangliosides. These compounds have been shown to increase efficacy of drug infusion, reduce fibrosis, prevent infection, and/or support neural growth.

Any of the drugs listed above, alone or in combination, or other drugs or combinations of drugs developed or shown to treat the effects of deafferentation may be applied to the stimulation site. In some embodiments, the one or more drugs are infused chronically into the stimulation site. Additionally or alternatively, the one or more drugs may be infused acutely into the stimulation site in response to a biological signal or a sensed need for the one or more drugs.

The stimulator (140) of FIG. 4 is illustrative of many types of stimulators that may be used to apply a stimulus to a stimulation site to treat the effects of deafferentation. For example, the stimulator (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus at a stimulation site within a patient. Exemplary IPGs suitable for use as described herein include, but are not limited to, those disclosed in U.S. Pat. Nos. 6,381,496; 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary cochlear implants suitable for use as described herein include, but are not limited to, those disclosed in U.S. Pat. Nos. 6,219,580; 6,272,382; and 6,308,101. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

Alternatively, the stimulator (140) may include an implantable microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 5:
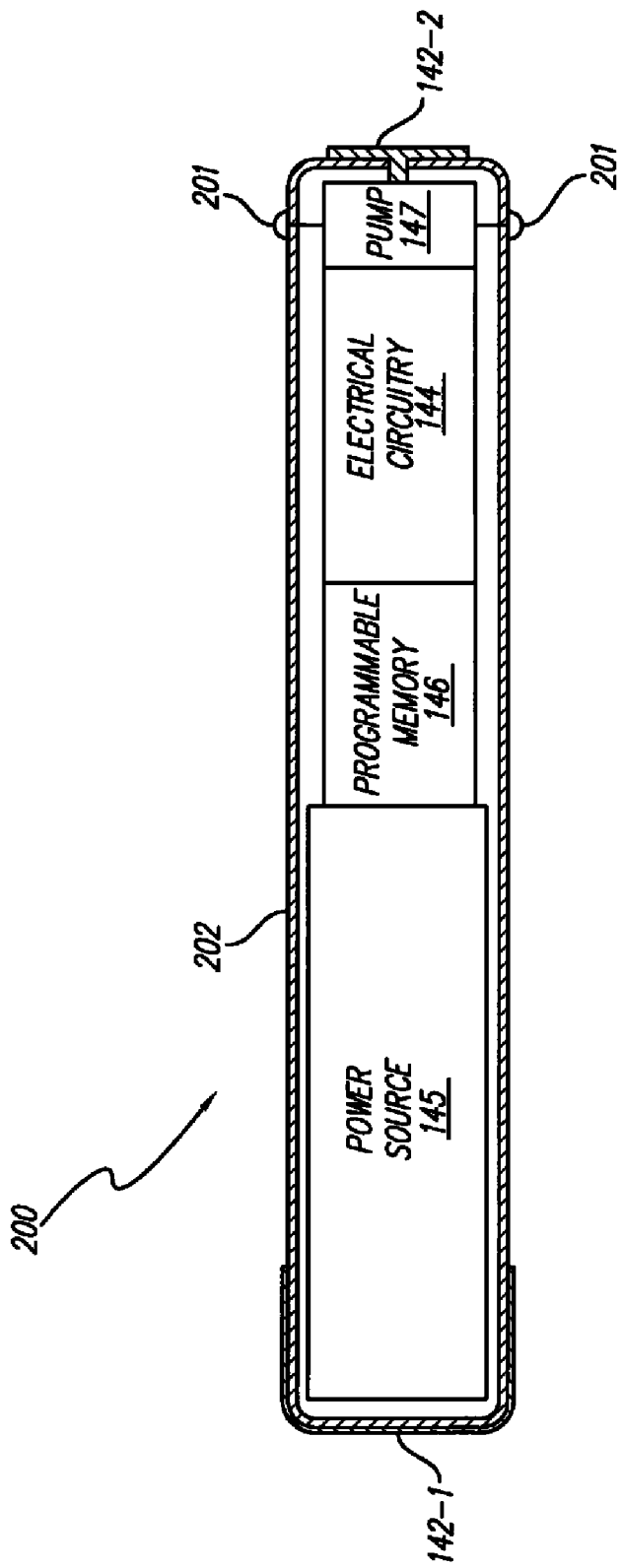
FIG. 5 illustrates an exemplary microstimulator that may be used as the stimulator according to principles described herein.

FIG. 5 illustrates an exemplary microstimulator (200) that may be used as the stimulator (140; FIG. 4) described herein. Other configurations of the microstimulator (200) are possible, as shown in the above-referenced patents and as described further below.

As shown in FIG. 5, the microstimulator (200) may include the power source (145), the programmable memory (146), the electrical circuitry (144), and the pump (147) described in connection with FIG. 4. These components are housed within a capsule (202). The capsule (202) may be a thin, elongated cylinder or any other shape as best serves a particular application. The shape of the capsule (202) may be determined by the structure of the desired target nerve, the surrounding area, and the method of implantation. In some embodiments, the volume of the capsule (202) is substantially equal to or less than three cubic centimeters. In some embodiments, the microstimulator (200) may include two or more leadless electrodes (142) disposed on the outer surface of the microstimulator (200).

The external surfaces of the microstimulator (200) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator (200) may also include one or more infusion outlets (201). The infusion outlets (201) facilitate the infusion of one or more drugs at a stimulation site to treat the effects of deafferentation. The infusion outlets (201) may dispense one or more drugs directly to the treatment site. Alternatively, catheters may be coupled to the infusion outlets (201) to deliver the drug therapy to a treatment site some distance from the body of the microstimulator (200). The stimulator (200) of FIG. 5 also includes electrodes (142-1 and 142-2) at either end of the capsule (202). One of the electrodes (142) may be designated as a stimulating electrode to be placed close to the treatment site and one of the electrodes (142) may be designated as an indifferent electrode used to complete a stimulation circuit.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques.

Figure 6:
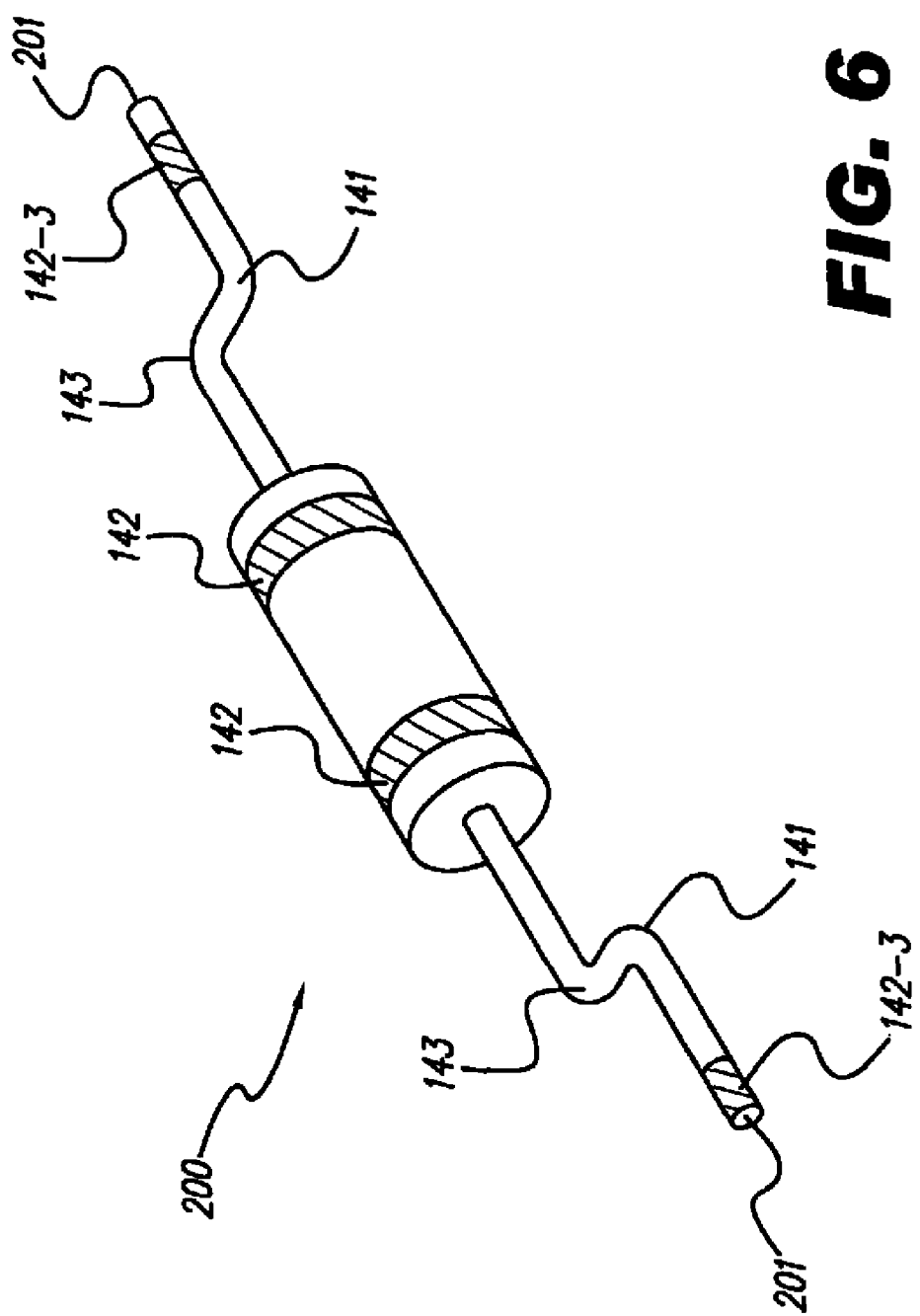
FIG. 6 shows one or more catheters coupled to a microstimulator according to principles described herein.

FIG. 6 shows an example of a microstimulator (200) with one or more catheters (143) coupled to the infusion outlets on the body of the microstimulator (200). With the catheters' (143) in place, the infusion outlets (201) that actually deliver the drug therapy to target tissue are located at the ends of catheters (143). Thus, in the example of FIG. 6, a drug therapy is expelled by the pump (147, FIG. 5) from an infusion outlet (201, FIG. 5) in the casing (202, FIG. 5) of the microstimulator (200), through the catheter (143), out an infusion outlet (201) at the end of the catheter (143) to the stimulation site within the patient. As shown in FIG. 6, the catheters (143) may also serve as leads (141) having one or more electrodes (142-3) disposed thereon. Thus, the catheters (143) and leads (141) of FIG. 6 permit infused drugs and/or electrical stimulation current to be directed to a stimulation site while allowing most elements of the microstimulator (200) to be located in a more surgically convenient site. The example of FIG. 6 may also include leadless electrodes (142) disposed on the housing of the microstimulator (200), in the same manner described above.

Figure 7:
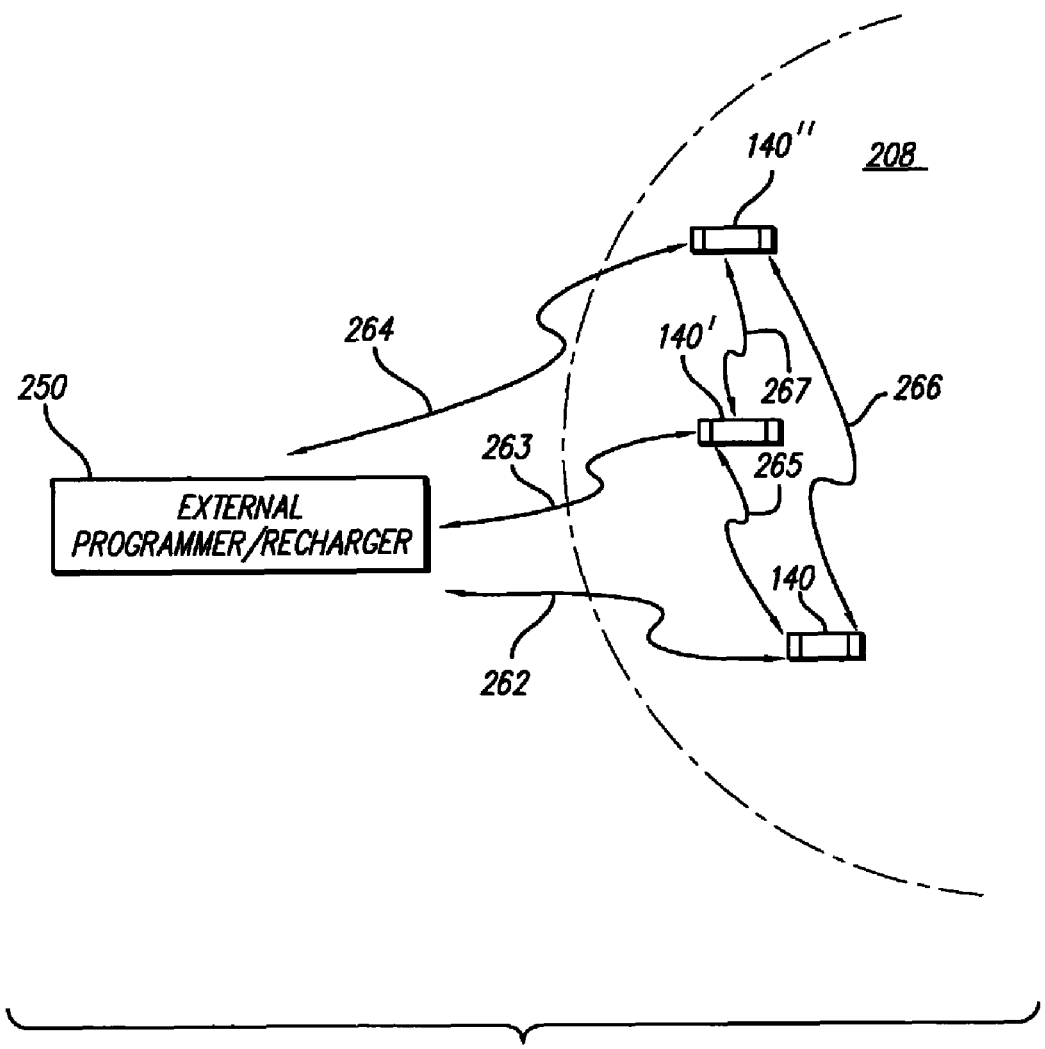
FIG. 7 depicts a number of stimulators configured to communicate with each other and/or with one or more external devices according to principles described herein.

Returning to FIG. 4, the stimulator (140) may be configured to operate independently. Alternatively, as shown in FIG. 7 and described in more detail below, the stimulator (140) may be configured to operate in a coordinated manner with one or more additional stimulators, other implanted devices, or other devices external to the patient's body. For a first stimulator may control, or operate under the control of, a second stimulator, other implanted device, or other device external to the patient's body. The stimulator (140) may be configured to communicate with other implanted stimulators, other implanted devices, or other devices external to the patient's body via an RF link, an ultrasonic link, an optical link, or any other type of communication link. For example, the stimulator (140) may be configured to communicate with an external remote control unit that is configured to send commands and/or data to the stimulator (140) and that is configured to receive commands and/or data from the stimulator (140).

In order to determine the strength and/or duration of electrical stimulation and/or amount and/or type(s) of stimulating drug(s) required to most effectively treat the effects of deafferentation, various indicators of the effects of deafferentation and/or a patient's response to treatment may be sensed or measured. These indicators include, but are not limited to, electrical activity of the brain (e.g., EEG); neurotransmitter levels; hormone levels; metabolic activity in the brain; blood flow rate in the head, neck or other areas of the body; medication levels within the patient; patient or caregiver input, e.g., the stimulation may be in response to a perceived sensation as described by the patient; temperature of tissue at the stimulation site; and/or brain hyperexcitability, e.g., increased response of given tissue to the same input. In some embodiments, the stimulator (140) may be configured to adjust the stimulation parameters in a closed loop manner in response to these measurements. The stimulator (140) may be configured to perform the measurements. Alternatively, other sensing devices may be configured to perform the measurements and transmit the measured values to the stimulator (140). Exemplary sensing devices include, but are not limited to, chemical sensors, electrodes, optical sensors, mechanical (e.g., motion, pressure) sensors, and temperature sensors.

Thus, one or more external devices may be provided to interact with the stimulator (140), and may be used to accomplish at least one or more of the following functions:

Function 1: If necessary, transmit electrical power to the stimulator (140) in order to power the stimulator (140) and/or recharge the power source (145).

Function 2: Transmit data to the stimulator (140) in order to change the stimulation parameters used by the stimulator (140).

Function 3: Receive data indicating the state of the stimulator (140) (e.g., battery level, drug level, stimulation parameters, etc.).

Additional functions may include adjusting the stimulation parameters based on information sensed by the stimulator (140) or by other sensing devices.

By way of example, an exemplary method of treating the effects of deafferentation may be carried out according to the following sequence of procedures. The steps listed below may be modified, reordered, and/or added to as best serves a particular application.

1. A stimulator (140) is implanted so that its electrodes (142) and/or infusion outlet (149) are coupled to or located near a stimulation site within the patient. If the stimulator (140) is a microstimulator, such as the microstimulator (200) described in FIG. 5, the microstimulator itself may be coupled to the stimulation site.

2. The stimulator (140) is programmed to apply at least one stimulus to the stimulation site. The stimulus may include electrical stimulation, drug stimulation, gene infusion, chemical stimulation, thermal stimulation, electromagnetic stimulation, mechanical stimulation, and/or any other suitable stimulation.

3. When the patient desires to invoke stimulation, the patient sends a command to the stimulator (140) (e.g., via a remote control) such that the stimulator (140) delivers the prescribed stimulation. The stimulator (140) may additionally or alternatively be configured to automatically apply the stimulation in response to sensed indicators of the effects of deafferentation.

4. To cease stimulation, the stimulator (140) may be turned off (e.g., via a remote control).

5. Periodically, the power source (145) of the stimulator (140) is recharged, if necessary, in accordance with Function 1 described above.

In alternative examples, the treatment administered by the stimulator (140), i.e., drug therapy and/or electrical stimulation, may be automatic and not controlled or invoked by the patient.

For the treatment of different patients, it may be desirable to modify or adjust the algorithmic functions performed by the implanted and/or external components, as well as the surgical approaches. For example, in some situations, it may be desirable to employ more than one stimulator (140), each of which could be separately controlled by means of a digital address. Multiple channels and/or multiple patterns of stimulation may thereby be used to deal with multiple effects of deafferentation.

As shown in the example of FIG. 7, a first stimulator (140) implanted beneath the skin of the patient (208) provides a stimulus to a first location; a second stimulator (140') provides a stimulus to a second location; and a third stimulator (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. stimulator (140), may control, or operate under the control of, another implanted device(s), e.g. stimulator (140') and/or stimulator (140"). Control lines (262-267) have been drawn in FIG. 7 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple stimulators (140) operating in a coordinated manner, the first and second stimulators (140, 140') of FIG. 7 may be configured to sense various indicators of a medical condition and transmit the measured information to the third stimulator (140"). The third stimulator (140") may then use the measured information to adjust its stimulation parameters and apply stimulation to a stimulation site accordingly. The various implanted stimulators may, in any combination, sense indicators of the medical condition, communicate or receive data on such indicators, and adjust stimulation parameters accordingly.

Alternatively, the external device (250) or other external devices communicating with the external device may be configured to sense various indicators of a patient's condition. The sensed indicators may then be collected by the external device (250) for relay to one or more of the implanted stimulators or may be transmitted directly to one or more of the implanted stimulators by any of an array of external sensing devices. In either case, the stimulator, upon receiving the sensed indicator(s), may adjust stimulation parameters accordingly. In other examples, the external controller (250) may determine whether any change to stimulation parameters is needed based on the sensed indicators. The external device (250) may then signal a command to one or more of the stimulators to adjust stimulation parameters accordingly.

The stimulator (140) of FIG. 4 may be implanted within a patient using any suitable surgical procedure such as, but not limited to, small incision, open placement, laparoscopy, or endoscopy. Exemplary methods of implanting a microstimulator, for example, are described in U.S. Pat. Nos. 5,193,539; 5,193,540; 5,312,439; 6,185,452; 6,164,284; 6,208,894; and 6,051,017. Exemplary methods of implanting an SCS, for example, are described in U.S. Pat. Nos. 5,501,703; 6,487,446; and 6,516,227. Exemplary methods of implanting a deep brain stimulator, for example, are described in U.S. Pat. Nos. 5,938,688; 6,016,449; and 6,539,263. All of these listed patents are incorporated herein by reference in their respective entireties.

Figure 8:
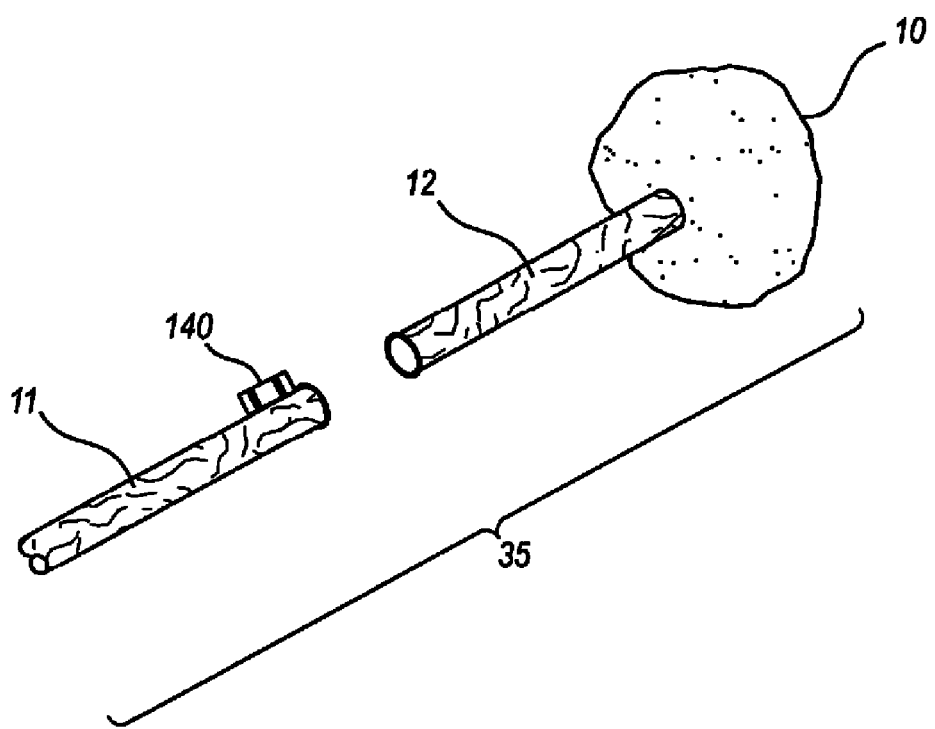
FIG. 8 illustrates a stimulator that has been implanted near the site of deafferentation according to principles described herein.

By way of example, FIG. 8 shows a stimulator (140) that has been implanted near the site of deafferentation. As shown in FIG. 8, the stimulator may be coupled directly to a deafferentated nerve (35). Alternatively, a lead and/or catheter may be implanted at the site of deafferentation and connected to an implanted stimulator (140) located elsewhere so that the bulk of the stimulator (140) may be implanted in a more convenient location. The stimulator (140) stimulates the proximal portion of the nerve (11) that is still in contact with the brain or central nervous system.

In some examples, the stimulator (140) of FIG. 8 may be configured to generate a stimulus that mimics the sensory input of the missing, de-enervated or dysfunctional end organ (10). It is believed that the mimicked sensory input provided by the stimulator (140) may prevent the brain from reorganizing its neural structure to compensate for the missing stimulus that should be received from the end organ (10).

For example, a normal body part typically provides sensory input to the central nervous system through action potentials in sensory neurons. The neurons fire in two patterns: tonic and phasic. Tonic activity includes a low-level, constant background firing to indicate to the central nervous system that the body part is present and/or functioning properly. Phasic activity, on the other hand, indicates that something is happening, e.g., the body part is moving. Hence, the stimulator (140) may be configured to mimic tonic and/or phasic activity in order to treat the effects of deafferentation. For example, the stimulator (140) may be implanted such that its electrodes are coupled to or near an end organ (10) affected by deafferentation. The stimulation parameters may then be programmed such that the stimulator (140) provides constant stimulation at the same amplitude, pattern, and rate as normal tonic activity that would originate from the affected end organ (10). In this manner, the patient's brain would sense that the affected site is functioning normally and would be prevented from reorganizing its neural structure to compensate for the affected end organ (10).

To illustrate, suppose a particular patient's leg is amputated. The proprioception system normally signals to the brain indicating where the leg is in space by assessing joint angles and muscle tension. The stimulator (140) may be configured to mimic proprioceptive activity after amputation by sending signals to the brain that indicate that the leg is where it is supposed to be in space. In some patients, the tonic activity of nerve fibers within a leg are between 60 to 100 Hz: Hence, the stimulator (140) may be configured to apply a stimulation of anywhere between 60 to 100 Hz as best serves the particular patient. The amplitude of the stimulation may commence at a low level and may be increase in small steps to the highest level that is comfortable to the patient. It will be recognized that the frequency and amplitude of the stimulation applied by the stimulator (140) may have any value as best serves a particular application. It will also be recognized that the frequency and amplitude of the stimulation may be adjusted on a periodic basis to prevent accommodation.

Figure 9:
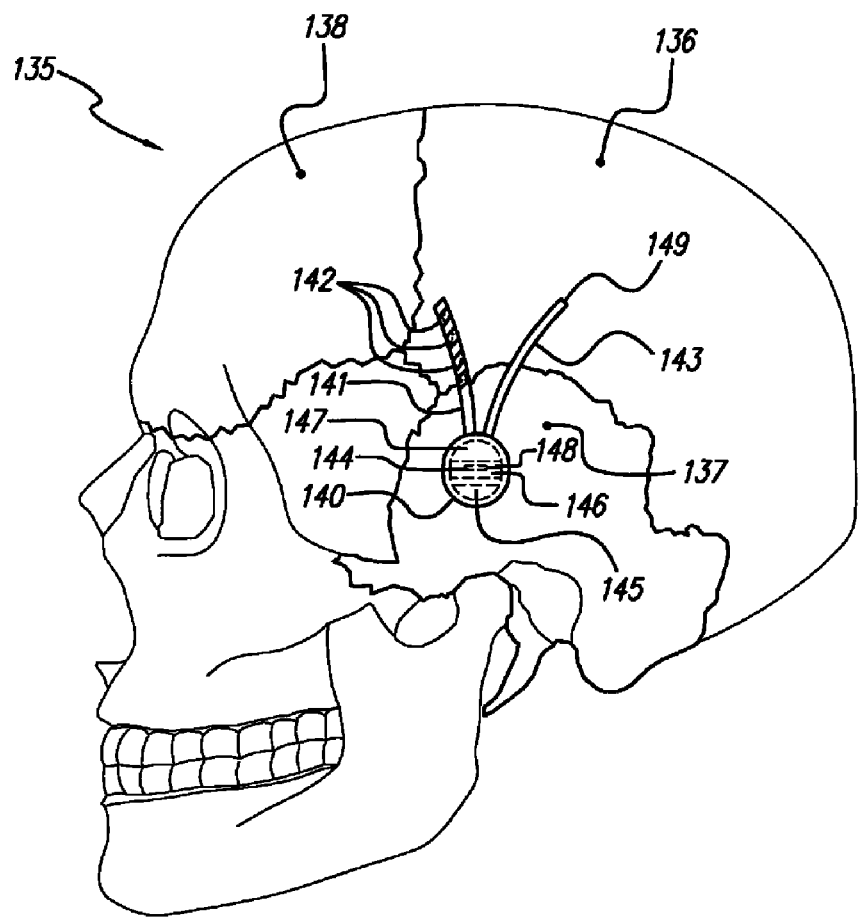
FIG. 9 illustrates a stimulator that has been implanted beneath the scalp of a patient to stimulate a stimulation site within the brain according to principles described herein.

As mentioned, the stimulus may additionally or alternatively be applied directly to the brain following loss of sensory input from the deafferentated nerve (35). FIG. 9 shows a stimulator (140) (e.g., a deep brain stimulator) that has been implanted beneath the scalp of a patient to apply a stimulus directly to the brain in order to treat the effects of deafferentation. The stimulator (140) may be implanted in a surgically-created shallow depression or opening in the skull (135). For instance, the depression may be made in the parietal bone (136), temporal bone (137), frontal bone (138), or any other bone within the skull (135) as best serves a particular application. The stimulator (140) may conform to the profile of surrounding tissue(s) and/or bone(s), thereby minimizing the pressure applied to the skin or scalp. Additionally or alternatively, the stimulator (140) may be implanted in a subdural space over any of the lobes of the brain, in a sinus cavity, or in an intracerebral ventricle.

In some examples, as shown in FIG. 9, a lead (141) and/or catheter (143) may run subcutaneously to an opening in the skull (135) and pass through the opening into or onto a stimulation site in the brain. Alternatively, the stimulator (140) is leadless and is configured to generate a stimulus that passes through the skull. In this manner, the brain may be stimulated without having to physically invade the brain itself.

Figure 10:
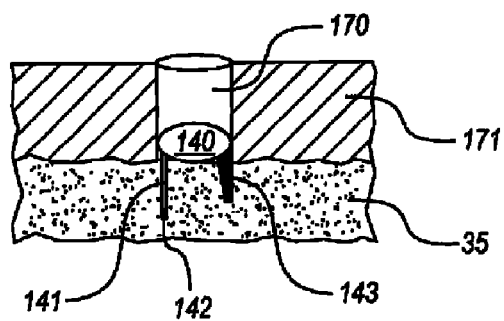
FIG. 10 is cross-sectional view of a stimulator implanted within a hole created in the skull of a patient according to principles described herein.

Alternatively, as shown in the cross-sectional view of FIG. 10, the stimulator (140) may be implanted within the lumen of a hole (170) created in the skull (171) and configured to apply a stimulus to a stimulation site within the brain (e.g., the cerebral cortex (30)). The hole (170) may be a burr hole, for example, and may be created with a surgical drill or any other suitable device. The hole (171) extends at least partially into the skull (171), and, as shown in FIG. 10, may extend all the way through the skull (171). The stimulator (140) is placed within the lumen of the hole (170) and coupled to the walls of the hole (170) and/or the top surface of the stimulation site, e.g., the cerebral cortex (30), using an adhesive, suture, or any other fastening device. Once the stimulator (140) has been implanted, the hole (170) may be covered by an appropriately sized cap (not shown).

As shown in FIG. 10, a lead (141) may be coupled to the stimulator (140) with the distal end of the lead (141) being routed to a particular location within the cerebral cortex (30) or other stimulation site in the brain. The distal end of the lead (141) may include one or more electrodes (142) configured to deliver an electrical stimulation current to the stimulation site. A catheter (143) may additionally or alternatively be coupled to the stimulator (140) and routed to the stimulation site so as to deliver one or more drugs at the stimulation site.

Figure 11A:
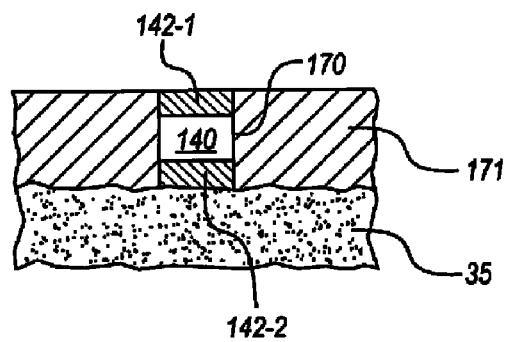
FIG. 11A is a cross-sectional view of a stimulator having two ring-like electrodes disposed on its surface implanted within a hole created in the skull of a patient according to principles described herein.
Figure 11B:
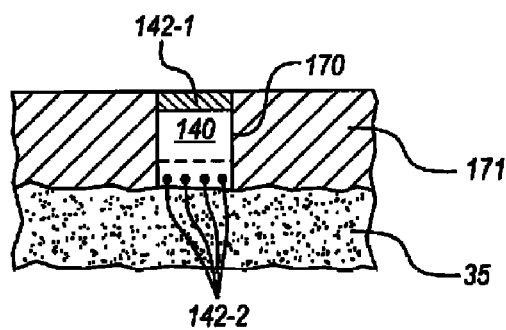
FIG. 11B is a cross-sectional view of a stimulator having multiple electrodes disposed thereon implanted within a hole created in the skull of a patient according to principles described herein.

As mentioned, the stimulator (140) may be leadless. FIGS. 11A-11B are cross sectional views of exemplary leadless stimulators (140) that have been implanted within the lumen of a hole (170) created in the skull (171). In this manner, the stimulation site within the brain may be stimulated without having to physically invade the brain itself.

For example, FIG. 11A shows an exemplary stimulator (140) with two ring-like electrodes (142) disposed on its surface. The electrode (142-2) more proximal to the stimulation site, e.g., the cerebral cortex (30), may be configured to act as a stimulating electrode while the electrode (142-2) more distal to the stimulation site may be configured to act as the indifferent electrode.

FIG. 11B shows an alternative electrode arrangement wherein the end most proximal to the stimulation site includes multiple electrodes (142-2) disposed thereon. Each electrode (142-2) may be selectively configured to act as either an anode or cathode so that monopolar and/or multipolar stimulation may be applied to the stimulation site. The distal end of the stimulator (140) may also include a selectively programmable electrode (142-1).

It is believed that the stimulation provided by the stimulator (140) may additionally or alternatively be configured to treat the effects of deafferentation by preventing the formation of neuromas. As mentioned, neuromas are painful nodular proliferations of nerve tissue that result from the futile attempt of a proximal nerve fiber to reunite with its corresponding severed distal severed portion. It is believed that neuromas may be in part responsible for one or more deafferentation effects. The stimulation provided by the stimulator (140) may prevent the formation of neuromas by mimicking sensory input from the severed distal portion, as described above. Hence, by preventing the formation of neuromas, the stimulation provided by the stimulator (140) may serve to alleviate one or more deafferentation effects.

The stimulation provided by the stimulator (140) may additionally or alternatively be configured to treat the effects of deafferentation by preventing the reorganization of A- and C-fiber terminals in the spinal cord. These terminals are often reorganized following deafferentation and may be in part responsible for the effects of deafferentation. Hence, it is believed that by mimicking sensory input from a deafferentated nerve, the stimulation provided by the stimulator (140) may prevent the reorganization of A- and C-fiber terminals in the spinal cord and thereby alleviate one or more deafferentation effects.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating one or more effects of deafferentation caused by the lack of sensory input of a missing or dysfunctional end organ of a patient, said method comprising:
generating a stimulus in accordance with one or more stimulation parameters that mimic a normal tonic activity that would originate from said end organ, wherein said stimulus matches an amplitude, pattern, and rate of said normal tonic activity that would originate from said end organ; and
applying said stimulus to a stimulation site within said patient, thereby treating said one or more effects of deafferentation.

2. The method of claim 1, wherein said stimulus prevents a brain of said patient from reorganizing a number of neural connections within said brain to compensate for said deafferentation.

3. The method of claim 1, where said one or more stimulation parameters comprises a frequency of about 60 to 100 Hertz.

4. The method of claim 1, where said one or more effects of said deafferentation comprise at least one or more of pain associated with said deafferentation, a phantom limb syndrome, a phantom auditory experience associated with said deafferentation, deafness, a phantom visual effect associated with said deafferentation, and blindness.

5. The method of claim 1, wherein said stimulus comprises an electrical stimulation current.

6. The method of claim 1, wherein said stimulus comprises one or more drugs.

7. The method of claim 1, further comprising sensing at least one indicator related to said one or more effects of said deafferentation and using said at least one sensed indicator to adjust said one or more of said stimulation parameters.

8. The method of claim 1, wherein said stimulation site comprises at least one of a location within a brain and a spinal cord of said patient.

9. The method of claim 8, wherein said location comprises at least one of a temporal lobe, a frontal lobe, a occipital lobe, a parietal lobe, a limbic system structure, a cerebellum, a brainstem, a cerebral cortex, a cochlear nerve, a visual cortex, an optic radiation, a Brodmann's area, a superior olivary complex, an inferior colliculus, an auditory cortex, and a cerebral ventricle.

10. A method of treating one or more effects of deafferentation caused by the lack of sensory input of a missing or dysfunctional end organ of a patient, the method comprising:
   implanting a stimulator within said patient;
   programming said stimulator with one or more stimulation parameters; and
   applying at least one stimulus with said stimulator to a stimulation site within said patient in accordance with said one or more stimulation parameters, wherein said stimulus matches an amplitude, pattern, and rate of said normal tonic activity that would originate from said end organ;
   wherein said one or more stimulation parameters and resulting stimulus are configured to mimic a normal tonic activity that would originate from said end organ, thereby treating said one or more effects of deafferentation.

11. The method of claim 10, wherein said one or more stimulation parameters are configured to cause said stimulus to prevent a brain of said patient from reorganizing a number of neural connections within said brain to compensate for said deafferentation.

12. The method of claim 1, wherein said one or more stimulation parameters comprises a frequency of about 60 to 100 Hertz.

13. The method of claim 10, further comprising sensing at least one indicator related to said one or more effects of said deafferentation and using said at least one sensed indicator to adjust one or more of said stimulation parameters.

14. The method of claim 10, wherein said stimulation site comprises at least one of a location within a brain and a spinal cord of said patient.

15. The method of claim 14, wherein said location comprises at least one of a temporal lobe, a frontal lobe, a occipital lobe, a parietal lobe, a limbic system structure, a cerebellum, a brainstem, a cerebral cortex, a cochlear nerve, a visual cortex, an optic radiation, a Brodmann's area, a superior olivary complex, an inferior colliculus, an auditory cortex, and a cerebral ventricle.

* * * * *